(12) United States Patent
Ciambecchini et al.

(10) Patent No.: US 8,445,716 B2
(45) Date of Patent: May 21, 2013

(54) METHOD FOR PREPARING FESOTERODINE AND/OR FESOTERODINE FUMARATE

(75) Inventors: Umberto Ciambecchini, Patrica (IT); Elio Ullucci, Patrica (IT); Stefano Turchetta, Patrica (IT); Maurizio Zenoni, Patrica (IT)

(73) Assignee: Chemi S.p.A., Cinisello Balsamo (MI) (IT)

( * ) Notice: Subject to any disclaimer, the term of this patent is extended or adjusted under 35 U.S.C. 154(b) by 374 days.

(21) Appl. No.: 12/779,268

(22) Filed: May 13, 2010

(65) Prior Publication Data

US 2010/0292503 A1 Nov. 18, 2010

(30) Foreign Application Priority Data

May 15, 2009 (IT) .............................. MI2009A0843

(51) Int. Cl.
*C07C 67/14* (2006.01)
(52) U.S. Cl.
USPC ........................................................ 560/140
(58) Field of Classification Search
USPC ........................................................ 560/140
See application file for complete search history.

(56) References Cited

U.S. PATENT DOCUMENTS 6,858,650 B1 * 2/2005 Meese ........................... 514/530

OTHER PUBLICATIONS

Search Report for Italian Application No. MI2009A000843, dated Nov. 6, 2009.

* cited by examiner

*Primary Examiner* — Joseph Kosack
*Assistant Examiner* — Matthew Coughlin
(74) *Attorney, Agent, or Firm* — Lucas & Mercanti, LLP

(57) ABSTRACT

A process is described for preparing fesoterodine and/or fesoterodine fumarate comprising the esterification of (R)-feso deacyl with isobutyric acid or a precursor thereof, such as an isobutyryl halide or the isobutyric acid anhydride to give fesoterodine, in a mixture of water at alkaline pH and/or at least one organic solvent. This process allows obtaining products with high yields and purities, and in particular a product having a content of (R)-2-[3-(diisopropylamino)-1-phenyl-propyl]-4-isobutyroyloxymethyl-phenyl isobutyrate less than 1% by mole and a content of (R)-2-[3-(diisopropylamino)-1-phenylpropyl]-4-(hydroxymethyl)phenol less than 0.05% by mole.

20 Claims, No Drawings

METHOD FOR PREPARING FESOTERODINE AND/OR FESOTERODINE FUMARATE

CROSS-REFERENCE TO RELATED APPLICATIONS

This application claims priority to and benefit of Italian Application No. MI2009A000843 filed on May 15, 2009, the content of which is incorporated herein by reference in its entirety.

FIELD OF THE INVENTION

The present invention has as object a process for preparing fesoterodine and/or fesoterodine fumarate comprising the esterification of (R)-feso deacyl with isobutyric acid or a precursor thereof, in a mixture of water at alkaline pH and/or at least one organic solvent.

BACKGROUND OF THE INVENTION

Fesoterodine fumarate is the international nonproprietary name (INN) of the active principle 2-((R)-3-diisopropylammonium-1-phenylpropyl)-4-(hydroxymethyl)phenylisobutyrate hydrogen fumarate, whose structure formula is reported herein below.

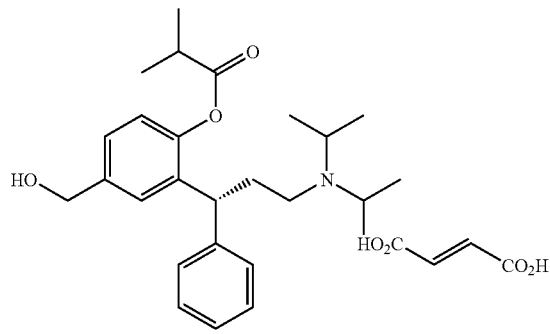

Fesoterodine fumarate was approved in Europe and in the U.S.A. for the treatment of overactive bladder syndrome with the commercial name of TOVIAZ®.

Fesoterodine fumarate was described for the first time in U.S. Pat. No. 6,858,650, which reports the preparation of the active ingredient for the salification of fesoterodine with fumaric acid, according to scheme 1 reported below.

Scheme 1

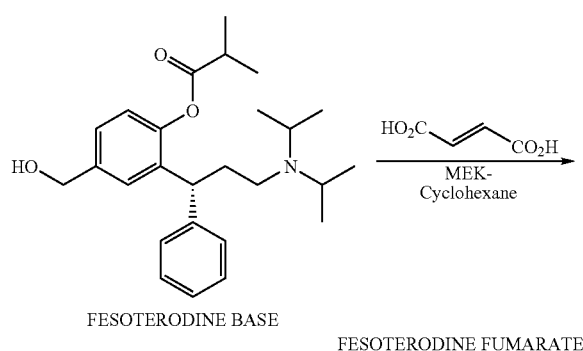

FESOTERODINE BASE

FESOTERODINE FUMARATE

In turn, fesoterodine (also called fesoterodine base) is described in U.S. Pat. No. 6,713,464, where it is prepared starting from a deacylated precursor, (R)-feso deacyl, i.e. (R)-2-[3-(diisopropylamino)-1-phenylpropyl]-4-(hydroxymethyl)phenol, according to scheme 2 reported herein below.

Scheme 2

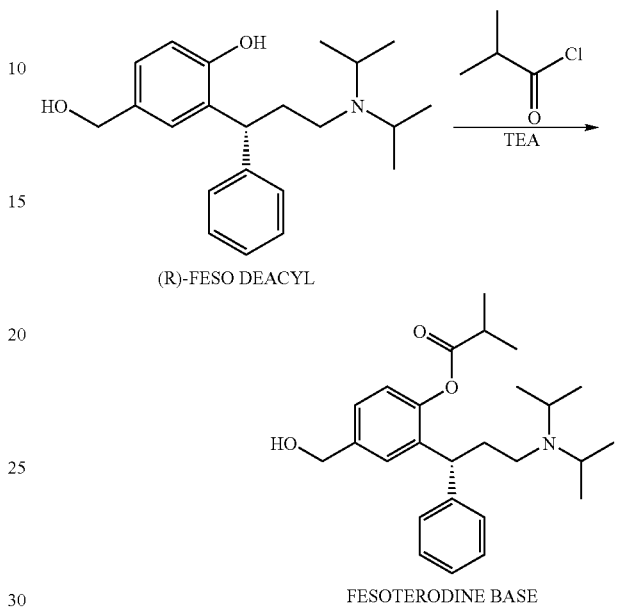

(R)-FESO DEACYL

FESOTERODINE BASE

The preparation of (R)-feso deacyl is instead described in U.S. Pat. No. 5,559,269.

As inferable from scheme 2, the transformation of (R)-feso deacyl into fesoterodine provides for the selective esterification of a phenolic hydroxyl in presence of an alcoholic hydroxyl; in the prior art (U.S. Pat. No. 6,713,464 and U.S. Pat. No. 6,858,650) such selective esterification is carried out at 0° C., with an exactly stoichiometric quantity of esterifying agent (isobutyryl chloride) and triethylamine, as scavenger of HCl generated by the esterification reaction. Fesoterodine thus obtained normally contains two typical impurities, i.e. the diesterification product, whose chemical name is (R)-2-[3-(diisopropylamino)-1-phenylpropyl]-4-isobutyroyloxymethyl-phenyl isobutyrate; and the starting product, i.e. (R)-feso deacyl.

WO2007140986 describes an improved esterification method with respect to U.S. Pat. No. 6,713,464 in which, in place of triethylamine, diisopropylethylamine (Hünig base) is used, which allows to improve the esterification selectivity. From table 1 of WO2007140986, it is possible to observe however that, even in the best proposed conditions (example 2), a diester quantity equal to 1.73% is formed, while in the conditions suggested by U.S. Pat. No. 6,713,464 (example 3) 5.90% diester is formed, and in absence of HCl scavenger bases (example 4) 2.90% diester is formed, while the starting product (Metabolite) remains non-reacted in a percentage equal to 2.9%.

There is therefore the need for a selective acylation method of (R)-feso deacyl which leads to fesoterodine (and thus to fesoterodine fumarate) with high yields and with a greater degree of purity, and in particular with a lower diester and (R)-feso deacyl content.

DETAILED DESCRIPTION OF THE INVENTION

During the experiments aimed at improving the selectivity conditions of the esterification reaction of (R)-feso deacyl, it was unexpectedly found that the use of a mixture constituted by alkaline water and at least one organic solvent allows carrying out the desired esterification in a very selective manner.

The discovered method also allows avoiding the use of amines such as triethylamine (TEA) or diisopropylethylamine (DIPEA) which, sharing common characteristics with fesoterodine in terms of basicity and solubility in the organic solvents, follow the product in the workup extractive steps and can constitute sources of impurities in the finished product.

In addition, such method above all allows obtaining a product (fesoterodine and/or fesoterodine fumarate) having purity characteristics definitely improved with respect to those of the prior art. In particular, the process of the present invention allows obtaining a product having a diester content less than 1% by mole, preferably less than 0.5%, and a content of (R)-feso deacyl less than 0.05% by mole, preferably less than 0.02%.

Therefore, it is an object of the present invention a process for preparing fesoterodine and/or fesoterodine fumarate comprising the esterification of (R)-feso deacyl with butyric acid or a precursor thereof, to give fesoterodine, in water or in a mixture of water and at least one organic solvent; according to a preferred aspect, such process is carried out in a mixture of water at alkaline pH and at least one organic solvent. A further object of the present invention is fesoterodine obtainable from such process.

(R)-feso deacyl usable in the process of the present invention can be obtained according to one of the methods reported in the literature, for example according to the method reported in U.S. Pat. No. 5,559,269, incorporated herein by reference.

According to one aspect of the invention, the water having alkaline pH used in the aforesaid mixture has a pH comprised between 7 and 9, preferably between 8 and 8.5. Said alkaline pH is preferably obtained by means of carbonate, bicarbonate, monobasic phosphate, dibasic phosphate, tribasic phosphate, borate and/or carboxylate of alkaline metal and/or alkaline-earth metal, still more preferably of sodium and/or potassium; in the preferred embodiment of the invention, the alkalinizing agent is sodium bicarbonate According to a further aspect of the invention, said isobutyric acid precursor is an isobutyryl halide or the isobutyric acid anhydride; in its preferred embodiment, the esterification reaction is carried out with isobutyryl chloride.

According to a further aspect of the invention, the at least one organic solvent used in the aforesaid biphasic mixture has a number of carbon atoms comprised between 1 and 12, preferably between 1 and 6. It is preferably selected among aliphatic hydrocarbons, aromatic hydrocarbons, ethers, esters, ketones, halogenated solvents and nitriles; still more preferably, said aliphatic hydrocarbon is cyclohexane; said aromatic hydrocarbon is toluene; said ether is tetrahydrofuran; said ester is selected from isopropyl acetate and butyl acetate; said ketone is methylethylketone; said halogenated solvent is dichloromethane; said nitrile is acetonitrile.

According to a further aspect of the invention, butyric acid or a precursor thereof are used in molar ratios comprised between 0.9 and 1.5 (preferably between 1.0 and 1.1), with respect to (R)-feso deacyl; (R)-feso deacyl is used in a weight/volume ratio (g/l) comprised between 1 and 10, preferably between 3 and 7, with respect to the water; (R)-feso deacyl is used in a weight/volume (g/l) ratio comprised between 5 and 100, preferably between 20 and 30, with respect to said at least one organic solvent.

In detail, the process according to the present invention provides the esterification of (R)-feso deacyl by using:

1) a solution of alkaline pH water, which is brought in contact with a solution of (R)-feso deacyl in at least one organic solvent, with butyric acid or a precursor thereof added thereto, or;

2.) dissolving (R)-feso deacyl in at least one organic solvent, adding butyric acid or a precursor thereof to the solution, and adding to the solution thus obtained an aqueous solution at alkaline pH.

The mixture obtained both in case 1) and in case 2) is preferably maintained at a temperature comprised between 0 and +10° C., still more preferably between +3 and +7° C., under stirring.

The selective esterification is completed in about two hours, preferably in about one hour, at the end of which the reaction mixture is worked up by separating the phases, washing the organic phase and evaporating it to a residue; crude fesoterodine is thus obtained, which can then be transformed into fesoterodine fumarate without further purification, according to the methods known in the art, for example according to the method described in U.S. Pat. No. 6,858,650, incorporated herein by reference.

According to one aspect of the invention, the residue is taken up with a ketone, preferably methylethylketone, and fumaric acid is added in a quantity preferably comprised between 1 and 1.5 equivalents, still more preferably between 1 and 1.1 equivalents, with respect to the loaded (R)-feso deacyl, at a temperature not greater than +40° C. and preferably comprised between +20 and +40° C. Once the mixture is cooled, the fesoterodine fumarate is filtered, washed with a ketone, preferably methylethylketone, and dried under vacuum; a product meeting the ICH quality specifications is obtained.

The following examples clarify in detail the conditions used for obtaining fesoterodine and fesoterodine fumarate at high purity according to the present invention; such examples are intended as exemplifying and non-limiting of the present invention.

EXAMPLE 1

Preparation of Fesoterodine Fumarate

In a 2-liter reactor, 31.2 g of sodium bicarbonate and 1250 ml of deionized water (pH 8.1) are charged. Stirring is performed until complete dissolution of the salt. In a 10-liter reactor, 250 g of (R)-Feso deacyl and 7500 ml of dichloromethane are charged. Stirring is performed until complete dissolution is obtained. Then, the aqueous bicarbonate solution is added to the organic solution and the biphasic mixture is cooled at 5° C. 86 g of isobutyryl chloride are added dropwise on the mixture and the mixture is stirred again for one hour from the end of the addition. Then, 1250 ml of a solution of 5% w/w sodium bicarbonate in water are added to the reaction mixture and the mixture is heated at 20° C., still under stirring. The lower organic phase is separated and it is first washed with 2500 ml of a solution of 5% w/w sodium bicarbonate in water and then twice with 2×2500 ml of deionized water. The obtained organic phase is concentrated to a small volume and 1000 ml of 2-butanone are added thereto. The mixture is once again evaporated to half the initial volume, then 1000 ml of 2-butanone are added again and 80.4 g of fumaric acid are added to the solution. The suspension is heated at 35° C. until complete dissolution. It is cooled at 20° C. and the crystallization is triggered with seeds of crystalline fesoterodine fumarate. Stirring is maintained for 1 hour at 20°

C. and for 2 hours at 0° C. Then, the suspension is filtered over Buchner filter and the pad is washed with 600 ml of 2-butanone. 621 g of moist product are obtained, which are dried at t=35° C. for 15 hours, obtaining 331 g of crystalline fesoterodine fumarate (85.7% yield). The purity of the final product, i.e. fesoterodine fumarate, is 99.8% by mole, with (R)-feso deacyl not detectable and diester impurity 0.10% by mole. In addition, different analyses were carried out on the intermediate fesoterodine; such analyses showed a diester content less than or equal to 0.40% by mole and a content of (R)-feso deacyl less than or equal to 0.01% by mole.

EXAMPLE 2

Preparation of Fesoterodine Fumarate

In a 250 ml flask, 3.0 g of (R)-Feso deacyl and 60 ml of dichloromethane are charged. Stirring is performed until complete solution is obtained. The temperature of the solution is brought to 0-5° C. 1.02 g of isobutyryl chloride dissolved in 30 ml of dichloromethane are added dropwise on the mixture and the mixture is stirred again for ten minutes from the end of the addition. Then, 15 ml of a solution of 2.5% w/w sodium bicarbonate in water (pH 8.1) are added to the reaction mixture and the mixture is stirred at 0÷5° C. for another 2 hours. It is then allowed to warm to room temperature and the lower organic phase is separated, washing it first with 30 ml of a solution of 5% w/w sodium bicarbonate in water then twice with 2×50 ml of deionized water. The obtained organic phase is concentrated to a small volume and 30 ml of 2-butanone are added. The mixture is once again evaporated to half the initial volume, then another 30 ml of 2-butanone are added and 0.9 g of fumaric acid are added. The suspension is heated at 35° C. until complete dissolution is obtained. It is cooled at 20° C. and the crystallization is triggered with seeds of crystalline fesoterodine fumarate. Stirring is maintained for 1 hour at 20° C. and for 2 hours at 0° C. The suspension is filtered over Buchner filter and the pad is washed with 10 ml of 2-butanone. 3.41 g of moist product are obtained which are dried at t=35° C. for 15 hours, obtaining 3.13 g of crystalline fesoterodine fumarate (85.7% yield). The purity of the product is 99.8% by mole, with (R)-feso deacyl 0.12% by mole and diester impurity 0.07% by mole.

We claim:

1. A process for preparing fesoterodine comprising reacting (R)-2-[3-(diisopropylamino)-1-phenylpropyl]-4-(hydroxymethyl)phenol with isobutyric acid, or a precursor thereof, in water or in a mixture of water at alkaline pH and at least one organic solvent.

2. The process according to claim 1, wherein said water has a pH comprised between 7 and 9.

3. The process according to claim 2, wherein said water has a pH comprised between 8 and 8.5.

4. The process according to claim 1, wherein said alkaline pH is obtained via addition of carbonate, bicarbonate, monobasic phosphate, dibasic phosphate, tribasic phosphate, borate and/or carboxylate of alkaline metal and/or alkaline-earth metal.

5. The process according to claim 4, wherein said alkaline pH is obtained via addition of sodium bicarbonate.

6. The process according to claim 1, wherein said isobutyric acid precursor is an isobutyryl halide or the isobutyric acid anhydride.

7. The process according to claim 6, wherein said isobutyryl halide is isobutyryl chloride.

8. The process according to claim 1, wherein said at least one organic solvent has a number of carbon atoms comprised between 1 and 12.

9. The process according to claim 8, wherein said at least one organic solvent has a number of carbon atoms comprised between 1 and 6.

10. The process according to claim 8, wherein said organic solvent is selected from aliphatic hydrocarbons, aromatic hydrocarbons, ethers, esters, ketones, halogenated solvents and nitriles.

11. The process according to claim 10, wherein said aliphatic hydrocarbon is cyclohexane; said aromatic hydrocarbon is toluene; said ether is tetrahydrofuran; said ester is selected from isopropyl acetate and butyl acetate; said ketone is methylethylketone; said halogenated solvent is dichloromethane; and said nitrile is acetonitrile.

12. The process according to claim 1, wherein said isobutyric acid or the precursor thereof are used in molar ratios comprised between 0.9 and 1.5 with respect to (R)-2-[3-(diisopropylamino)-1-phenylpropyl]-4-(hydroxymethyl)phenol.

13. The process according to claim 12, wherein said isobutyric acid or the precursor thereof are used in molar ratios comprised between 1.0 and 1.1 with respect to (R)-2-[3-(diisopropylamino)-1-phenylpropyl]-4-(hydroxymethyl)phenol.

14. The process according to claim 1, wherein (R)-2-[3-(diisopropylamino)-1-phenylpropyl]-4-(hydroxymethyl)phenol is used in a weight/volume ratio (g/l) comprised between 1 and 10 with respect to the water and/or wherein (R)-2-[3-(diisopropylamino)-1-phenylpropyl]-4-(hydroxymethyl)phenol is used in a weight/volume ratio (g/l) comprised between 5 and 100 with respect to said at least one organic solvent.

15. The process s according to claim 14, wherein (R)-2-[3-(diisopropylamino)-1-phenylpropyl]-4-(hydroxymethyl)phenol is used in a weight/volume ratio (g/l) comprised between 3 and 7 with respect to the water and/or wherein (R)-2-[3-(diisopropylamino)-1-phenylpropyl]-4-(hydroxymethyl)phenol is used in a weight/volume ratio (g/l) comprised between 20 and 30 with respect to said at least one organic solvent.

16. The process according to claim 1, wherein the reaction mixture is maintained at a temperature comprised between 0 and +10° C.

17. The process according to claim 16, wherein the reaction mixture is maintained at a temperature comprised between +3 and +7° C.

18. The process according to claim 1 for preparing fesoterodine fumarate.

19. A process according to claim 1 for preparing fesoterodine and/or fesoterodine fumarate having a content of (R)-2-[3-(diisopropylamino)-1-phenylpropyl]-4-isobutyroyloxymethyl-phenyl isobutyrate less than 1% by mole and a content of (R)-2-[3-(diisopropylamino)-1-phenylpropyl]-4-(hydroxymethyl)phenol less than 0.05% by mole.

20. A process according to claim 1 for preparing fesoterodine and/or fesoterodine fumarate having a content of (R)-2-[3-(diisopropylamino)-1-phenylpropyl]-4-isobutyroyloxymethyl-phenyl isobutyrate less than 0.5% by mole and a content of (R)-2-[3-(diisopropylamino)-1-phenylpropyl]-4-(hydroxymethyl)phenol less than 0.02% by mole.

* * * * *